United States Patent [19]
Jones, Jr. et al.

[11] 4,144,228
[45] Mar. 13, 1979

[54] METHIONINE[5]-ENKEPHALIN SULFOXIDES AND SULFONES

[75] Inventors: David A. Jones, Jr., Evanston; James M. Schlatter, Glenview, both of Ill.

[73] Assignee: G. D. Searle & Co., Chicago, Ill.

[21] Appl. No.: 684,322

[22] Filed: May 7, 1976

[51] Int. Cl.$^2$ ............... C07C 103/52; A61K 37/00
[52] U.S. Cl. .................... 260/112.5 R; 424/177
[58] Field of Search ............ 260/112.5 R; 424/177

[56] References Cited

U.S. PATENT DOCUMENTS

| | | | |
|---|---|---|---|
| 3,853,838 | 12/1974 | Greven | 260/112.5 R |
| 3,856,770 | 12/1974 | Greven | 260/112.5 R |

OTHER PUBLICATIONS

Nature, 258, pp. 577–579 (1975).
Nature, 260, p. 624 (1976).
Nature, 260, p. 625 (1976).

*Primary Examiner*—Delbert R. Phillips
*Attorney, Agent, or Firm*—Michael Thomas Murphy

[57] ABSTRACT

Methionine[5]-enkephalin sulfoxides and sulfones having agonist activity at opiate receptors are disclosed herein. These sulfoxides and sulfones are useful as analgesics, non-addicting narcotic antagonists and anti-diarrheal agents.

6 Claims, No Drawings

METHIONINE[5]-ENKEPHALIN SULFOXIDES AND SULFONES

BACKGROUND OF THE INVENTION

This invention relates to methionine[5]-enkephalin sulfoxides and sulfones which display agonist activity at opiate receptors. These sulfoxides and sulfones are derivatives of methionine[5]-enkephalin, one of the two components of naturally occurring enkephalin. Methionine[5]-enkephalin is represented by the following formula

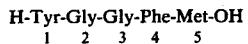

wherein the Tyr, Phe and Met amino acid residues are all of the L-stereochemical configuration.

SUMMARY OF THE INVENTION

The present invention is concerned with novel methionine[5]-enkephalin sulfoxides and sulfones. More particularly, this invention is concerned with compounds of the formula

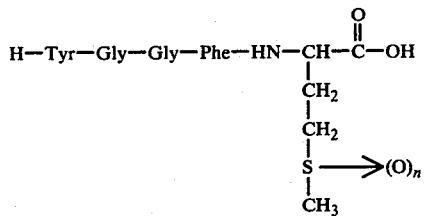

wherein n is the integer 1 or 2, and the stereochemical configuration of each of the optically active amino acids is D, L, or DL.

Preferred compounds of this invention are those of the formula

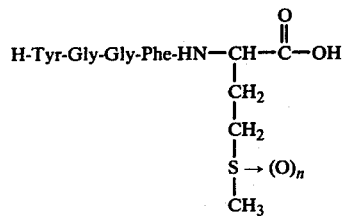

wherein n is as defined hereinbefore, and the stereochemical configuration of each of the optically active amino acids is L.

Abbreviations connote the amino acids defined in accordance with the nomenclature rules published by the IUPACIUB Commission on Biochemical Nomenclature in $Biochem.\ J.$, 126, 773–780 (1972). The amino acids have the L-stereochemical configuration unless otherwise indicated.

Equivalent to the enformulated compounds for the purposes of this invention are solvates thereof in which biologically insignificant amounts of solvent are present.

Also equivalent to the compounds of formula (I) for the purposes of this invention are the pharmaceutically acceptable acid addition salts thereof. Such acid addition salts can be derived from a variety of inorganic and organic acids such as sulfuric, phosphoric, hydrochloric, hydrobromic, hydriodic, nitric, sulfamic, citric, lactic, pyruvic, oxalic, maleic, succinic, tartaric, cinnamic, acetic, trifluoroacetic, benzoic, salicylic, gluconic, ascorbic and related acids.

DETAILED DESCRIPTION OF THE INVENTION

The compounds of the present invention are useful in consequence of their valuable pharmacological properties. They are, for example, agonists at opiate receptor sites. Such agonists are useful as analgesics, narcotic antagonists and anti-diarrheal agents.

The assay utilized for detection of the agonist activity at opiate receptor sites is a modification of the technique described by Pert, Snowman and Snyder, in $Brain\ Research$, 70, 184 (1974).

Details of that assay are as follows:

Guinea pigs weighing 600–700 grams are killed and the whole brains removed and homogenized in 0.32 M sucrose after removal of the cerebella. The homogenate is centrifuged at 1000 × g for ten minutes, the pellet discarded, and the supernatant fraction centrifuged at 17,500 × g for ten minutes. The pellet is osmotically shocked with ice-cold water and recentrifuged at 10,000 × g for ten minutes. The resultant supernatant, containing the membrane fraction used for the binding assay, is diluted with 0.05 M Tris buffer (pH 7.4 at 25° C.) to a protein concentration of 2 mg/ml.

Aliquots of the final membrane suspension are incubated with varying concentrations of the test compound. Aliquots incubated with $10^{-6}$ M levorphanol are used to determine non-specific binding of the radioactive ligand. The assay is run at 4° C. and is initiated with the addition of 8 mM $^3$H-naloxone (specific activity greater than 20 C/mmole). The reaction is terminated by rapid filtration of the incubation mixture on GF/B glass filter papers. The membranes trapped on the filter paper are washed twice with ice-cold Tris buffer. The amount of radioactive ligand bound is determined by liquid scintillation techniques. An $ID_{50}$ concentration of the $^3$H-naloxone binding is determined from log-probit curves of the percent inhibition of $^3$H-naloxone binding versus concentration of the test compound.

The in vitro assay described is widely known to correlate with relative agonist-antagonist properties in vivo; Nature, vol. 247, Jan. 11, 1974. When known agonists-antagonists such as morphine and methadone are tested by this assay, in the absence of sodium ion, they had $ID_{50}$ concentrations of $1.2 \times 10^{-8}$ and $2.4 \times 10^{-8}$, respectively.

It is also known that the receptor affinities in the ileum are similar in their binding characteristics with those of the brain; Lars Terenius, $Acta.\ Pharmacol.\ et\ Toxicol.$, 37, 211–221 (1975). Available evidence indicates that drugs which act on the ileum opiate receptors cause constipation, and are therefore useful as anti-diarrheal agents.

The compounds of formula (I) may be combined with various typical pharmaceutical carriers to provide compositions suitable for use as analgesics, as narcotic antagonists for use in the treatment of drug addiction and as anti-diarrheals. The dosage of these compounds is dependent upon various factors, such as the particular compound employed and the particular response obtained. Typical dosages for use as an analgesic vary from 0.1 to 6.0 mg./kg. per day administered parenterally.

The manufacture of the instant novel compounds is conveniently achieved by processes adapted to the synthesis of peptides, i.e. both solution synthesis and solid-phase peptide syntheses. In the case of solution synthesis the order in which the amino acids are coupled is not critical. Thus, the pentapeptides may be produced by coupling any two suitable units containing the desired amino acids.

A convenient method for preparing the compounds of this invention involves the coupling or an N-protected active ester of the formula

wherein □ represents an N-protecting group and X represents an active ester group, with the C-terminal methionine derivative, optionally substituted with protecting groups, of the formula

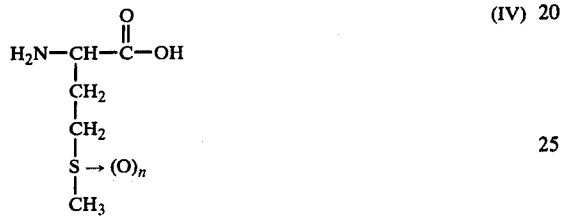

wherein n is defined hereinbefore, to afford the N-protected pentapeptide of the formula

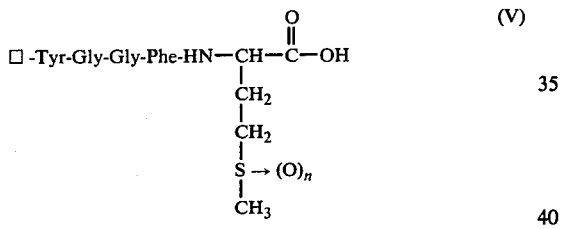

wherein □ and n are as defined hereinbefore. This pentapeptide is then deprotected in a conventional manner to afford the desired compounds of formula (I).

The above coupling reaction is conducted in suitable organic solvent. Typical solvents for use in this reaction include, but are not limited to, methylene chloride, dimethylformamide, and tetrahydrofuran. The use of an organic base, e.g., N-methylmorpholine facilitates the reaction.

Alternatively, the desired pentapeptide can be obtained by solid-phase peptide synthesis which consists of first attaching to a polymer support, e.g., a chloromethylated copolystyrene-1% divinylbenzene polymer, the optionally N-protected C-terminal methionine derivative, followed by removal of the N-protecting group, and coupling, in the presence of a suitable reagent, e.g., dicyclohexylcarbodiimide, successively with each of the appropriate N-protected amino acids.

Suitable active esters for use in this invention are those which cause the acid function of the amino acid to become more reactive such as alkyl esters with electron withdrawing (negative) substituents, vinyl esters, enol esters, phenyl esters, thiophenyl esters, nitrophenyl esters, 2,4-dinitrophenyl esters, trichlorophenyl esters, and nitrophenylthiol esters. The use of 2,4,5-trichlorophenyl esters is particularly preferred for the preparation of the present compounds.

The amino functions of the intermediates of this invention may be protected by commonly used amino protection groups such as aryl-lower alkyl groups, such as diphenylmethyl or triphenylmethyl groups, which are optionally substituted by halogen, nitro, lower alkyl or lower alkoxy, for example; benzhydryl, trityl, and di-paramethoxybenzhydryl; acyl groups, such as formyl, trifluoroacetyl, phthaloyl, p-toluenesulphonyl, benzenesulphonyl, benzenesulphenyl and o-nitrophenylsulphenyl; groups derived from carbonic acid or thiocarbonic acid, such as carbobenzoxy groups which are optionally substituted in the aromatic radical by halogen atoms, nitro groups or lower alkyl, lower alkoxy or lower carboalkoxy groups, for example, carbobenzoxy, p-bromocarbobenzoxy or p-chlorocarbobenzoxy, p-nitrocarbobenzoxy and p-methoxycarbobenzoxy; coloured benzyloxycarbonyl groups such as p-phenylazobenzyloxycarbonyl and p-(p'-methoxyphenylazo)benzyloxycarbonyl, tolyloxycarbonyl, 2-phenyl 2-propoxycarbonyl, 2-tolyl-2-propoxycarbonyl and 2-(parabiphenylyl)-2-propoxycarbonyl; and aliphatic oxycarbonyl groups, such as t-butoxycarbonyl, allyloxycarbonyl, cyclopentyloxycarbonyl, t-amyloxycarbonyl. A particularly preferred N-protecting group for use in this invention is the t-butoxycarbonyl group.

The amino groups can also be protected by forming enamines, obtained by reaction of the amino group with 1,3-diketones, for example benzoylacetone, or acetylacetone.

Protecting groups are conveniently removed by reactions such as reduction with sodium in liquid ammonium, hydrogenolysis (for instance, in the presence of a palladium black catalyst), treatment with a hydrohalo acid (such as hydrobromic, hydrofluoric or hydrochloric acids) in acetic acid, or treatment with trifluoroacetic acid.

The following examples describe in detail the preparation of compounds illustrative of the present invention. It will be apparent to those skilled in the art that many modifications, both of materials and methods, may be practiced without departing from the purpose and intent of this disclosure. Throughout the examples hereinafter set forth, temperatures are given in degrees Centigrade (° C.) and relative amounts in parts by weight, except as otherwise noted.

EXAMPLE 1

A solution of 19.5 parts N-butoxycarbonylglycine 2,4,5-trichlorophenyl ester and 12.8 parts L-phenylalanine benzyl ester in 200 parts methylene chloride is stirred overnight at room temperature. Completion of the reaction is determined by thin layer chromatography showing the disappearance of the phenylalanine benzyl ester spot. The solvent is then removed by evaporation under reduced pressure. The crude dipeptide is then subjected to low-pressure column chromatography on silica gel to afford N-t-butoxycarbonylglycyl-L-phenylalanine benzyl ester.

EXAMPLE 2

13.4 Parts N-t-butoxycarbonylglycyl-L-phenylalanine benzyl ester is dissolved in 200 parts dioxane and treated with a 10 fold excess of 2 N hydrochloric acid in dioxane for 10 minutes. Removal of the solvent under reduced pressure affords pure glycyl-L-phenylalanine benzyl ester hydrochloride.

EXAMPLE 3

A solution of 6.1 parts glycyl-L-phenylalanine benzyl ester hydrochloride, 7.0 parts N-t-butoxycarbonylglycine 2,4,5-trichlorophenyl ester and 1.8 parts N-methylmorpholine in 150 parts methylene chloride is stirred overnight at room temperature. The solvents are then removed by evaporation under reduced pressure to yield the crude tripeptide. Purification by low pressure column chromatography affords pure N-t-butoxycarbonylglycylglycyl-L-phenylalanine benzyl ester.

EXAMPLE 4

5.6 Parts N-t-butoxycarbonylglycylglycyl-L-phenylalanine benzyl ester is dissolved in 200 parts dioxane and contacted with a 10 fold excess of a 2 N solution of hydrochloric acid in dioxane for 10–15 minutes. Removal of the solvent under reduced pressure, followed by trituration with ethyl ether affords pure glycylglycly-L-phenylalanine benzyl ester.

EXAMPLE 5

A solution of 3.6 parts glycylglycly-L-phenylalanine benzyl ester hydrochloride, 0.94 part N-methylmorpholine and 4.6 parts N-t-butoxycarbonyl-L-tyrosine pentachlorophenyl ester in 135 parts methylene chloride is stirred overnight at room temperature. The solvent is then removed by evaporation under reduced pressure. The crude material is subjected to low-pressure column chromatography on silica gel to afford N-t-butoxycarbonyl-L-tyrosylglycylglycyl-L-phenylalanine benzyl ester.

EXAMPLE 6

To a solution of 3.6 parts N-t-butoxycarbonyl-L-tyrosylglycylglycyl-L-phenylalanine benzyl ester in 160 parts methanol is added 0.4 part palladium black metal catalyst. The resulting mixture is shaken with hydrogen at room temperature at atmospheric pressure for about 5 hours. The catalyst is then removed by filtration, and the solvent removed by evaporation under reduced pressure. The resulting crude material is purified using low-pressure chromatography to afford N-t-butoxycarbonyl-L-tyrosylglycylglycyl-L-phenylalanine.

EXAMPLE 7

10.84 Parts N-t-butoxycarbonyl-L-tyrosylglycylglycyl-L-phenylalanine and 2.0 parts N-methylmorpholine are dissolved in 200 parts dimethylformamide and cooled to −15° C. Then, 2.9 parts isobutyl chloroformate is added dropwise over a thirty minute period while keeping the temperature between −15° C. to −10° C. After the addition is completed, a solution of 3.3 parts L-methionine sulfoxide in 15 parts dimethylformamide is slowly added. The mixture is stirred for a further thirty minutes at −15° C. and then warmed to room temperature and stirred thereat for an additional 2 hours. The product is isolated by diluting the reaction mixture with 10 volumes water and extracting with ethyl acetate. The ethyl acetate extracts are combined, dried over anhydrous sodium sulfate and stripped of solvent under reduced pressure. The residue is purified by low-pressure chromatography to afford N-t-butoxycarbonyl-L-tyrosyl-glycylglycyl-L-phenylalanyl-L-methionine sulfoxide.

EXAMPLE 8

12.0 Parts N-t-butoxycarbonyl-L-tyrosylglycylglycyl-L-phenylalanyl-L-methionine sulfoxide is suspended in 100 parts by volume acetic acid and treated with 50 parts by volume 6 M HCl in dioxane. The resulting mixture is stirred at room temperature for two hours and then stripped of solvent under reduced pressure. Trituration of the residue with ether affords solid L-tyrosylglycylglycyl-L-phenylalanyl-L-methionine sulfoxide hydrochloride. This compound is represented by the following formula.

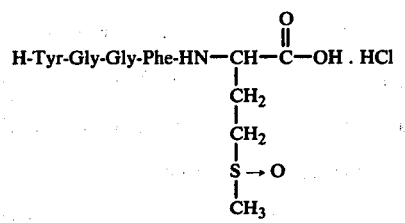

EXAMPLE 9

When an equivalent quantity of L-methionine sulfone is substituted for the L-methionine sulfoxide of Example 7, there is obtained N-t-butoxycarbonyl-L-tyrosylglycylglycyl-L-phenylalanyl-L-methionine sulfone.

EXAMPLE 10

Repetition of the procedure of Example 8 using an equivalent quantity of N-t-butoxycarbonyl-L-tyrosylglycylgly-cyl-L-phenylalanyl-L-methionine sulfone affords L-tyrosylgly-cylglycyl-L-phenylalanyl-L-methionine sulfone hydrochloride. This compound is represented by the following formula.

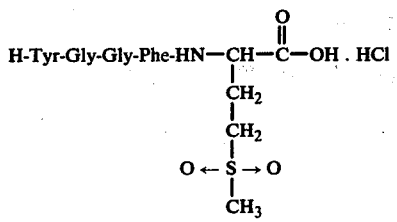

EXAMPLE 11

When equivalent quantities of N-t-butoxycarbonyl-D-tyrosylglycylglycyl-D-phenylalanine and D-methionine sulfoxide are substituted for the N-t-butoxycarbonyl-L-tyrosylglycylglycyl-L-phenylalanine and L-methionine sulfoxide in Example 7, and the procedure detailed therein substantially repeated, there is obtained N-t-butoxycarbonyl-D-tyrosylglycylglycyl-D-phenylalanyl-D-methionine sulfoxide.

EXAMPLE 12

Repetition of the procedure of Example 8 using an equivalent quantity of N-t-butoxycarbonyl-D-tyrosylglycylglycyl-D-phenylalanyl-D-methionine sulfoxide affords D-tyrosylglycylglycyl-D-phenylalanyl-D-methionine sulfoxide hydrochloride.

EXAMPLE 13

When equivalent quantities of N-t-butoxycarbonyl-DL-tyrosylglycylglycyl-DL-phenylalanine and DL-methionine sulfone are substituted for the N-t-butoxycarbonyl-L-tyrosylglycylglycyl-L-phenylalanine and L-methionine sulfoxide in Example 7, and the procedure detailed therein substantially repeated, there is obtained N-t-butoxycarbonyl-DL-tyrosylglycylglycyl-DL-phenylalanyl-DL-methionine sulfone.

EXAMPLE 14

Repetition of the procedure of Example 8 using an equivalent quantity of N-t-butoxycarbonyl-DL-tyrosylglycylglycyl-DL-phenylalanyl-DL-methionine sulfone affords DL-tyrosylglycylglycyl-DL-phenylalanyl-DL-methionine sulfone hydrochloride.

The hydrochloride salts in the preceding examples are readily converted into the respective free bases of the peptides by passing the compounds through an ion exchange column in an aqueous solution. Thus, when an aqueous solution containing L-tyrosylglycylglycyl-L-phenylalanyl-L-methionine sulfoxide hydrochloride is passed through an ion exchange column there is obtained L-tyrosylglycylglycyl-L-phenylalanyl-L-methionine sulfoxide.

What is claimed is:

1. A compound of the formula

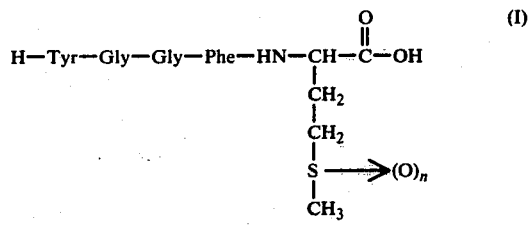

wherein n is the integer 1 or 2, and the stereochemical configuration of each of the optically active amino acids is D, L or DL.

2. A compound according to claim 1 of the formula

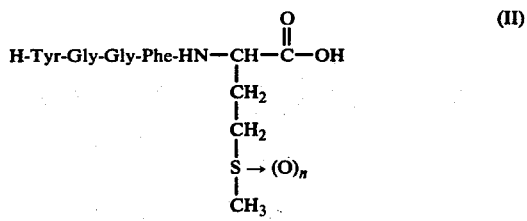

wherein n is the integer 1 or 2, and the stereochemical configuration of each of the optically active amino acids is L.

3. The compound according to claim 1 which is L-tyrosylglycylglycyl-L-phenylalanyl-L-methionine sulfoxide.

4. The compound according to claim 1 which is L-tyrosylglycylglycyl-L-phenylalanyl-L-methionine sulfone.

5. The compound according to claim 1 which is D-tyrosylglycylglycyl-D-phenylalanyl-D-methionine sulfoxide.

6. The compound according to claim 1 which is DL-tyrosylglycylglycyl-DL-phenylalanyl-DL-methionine sulfone.

* * * * *